United States Patent [19]

Kapmeyer

[11] Patent Number: 4,962,046
[45] Date of Patent: Oct. 9, 1990

[54] DISPERSION POLYMERS, AND THEIR USE
[75] Inventor: Wolfgang Kapmeyer, Marburg, Fed. Rep. of Germany
[73] Assignee: Behringwerke Aktiengesellschaft, Marburg, Fed. Rep. of Germany
[21] Appl. No.: 39,107
[22] Filed: Apr. 16, 1987
[30] Foreign Application Priority Data Apr. 18, 1986 [DE] Fed. Rep. of Germany ....... 3613111

[51] Int. Cl.$^5$ .......................................... G01N 33/546
[52] U.S. Cl. .................................... 436/533; 436/534; 524/812
[58] Field of Search ................................ 436/533–546, 436/805; 524/812; 534/15; 428/402

[56] References Cited

U.S. PATENT DOCUMENTS 4,563,431 1/1986 Pauly et al. .......................... 436/533
4,693,912 9/1987 Spadaro et al. ...................... 436/533
4,738,932 4/1988 Yabusaki ............................. 436/533
4,784,912 11/1988 Schaeffer et al. .................... 436/533

FOREIGN PATENT DOCUMENTS 1469358 4/1977 United Kingdom .

Primary Examiner—Christine M. Nucker
Assistant Examiner—T. J. Wallen
Attorney, Agent, or Firm—Finnegan, Henderson, Farabow, Garrett & Dunner

[57] ABSTRACT

The invention relates to dispersion polymers, processes for their preparation and their use, the dispersion polymers being obtained by a seed polymerization process in the presence of seed latices with a high residual monomer content and a monomer mixture of at least one compound of the formula I

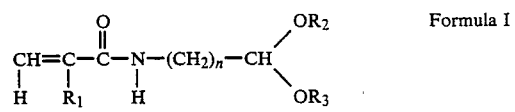

wherein $n = 1-6$;

$R_1 = H$ or $CH_3$ and $R_2$ and $R_3$ are identical or different, where $R_2$ and $R_3 = -(CH_2)_m-CH_3$, and $m = 0-7$, or

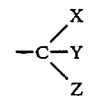

or $R_2$ and $R_3 =$ an aryl radical, and if appropriate acrylic acid, methacrylic acid, crotonic acid and monomers from which the seed latex is prepared.

The invention furthermore relates to the biologically active latex conjugates which are obtained using the dispersion polymers and are particularly suitable for serological and immunological determination methods.

8 Claims, 2 Drawing Sheets

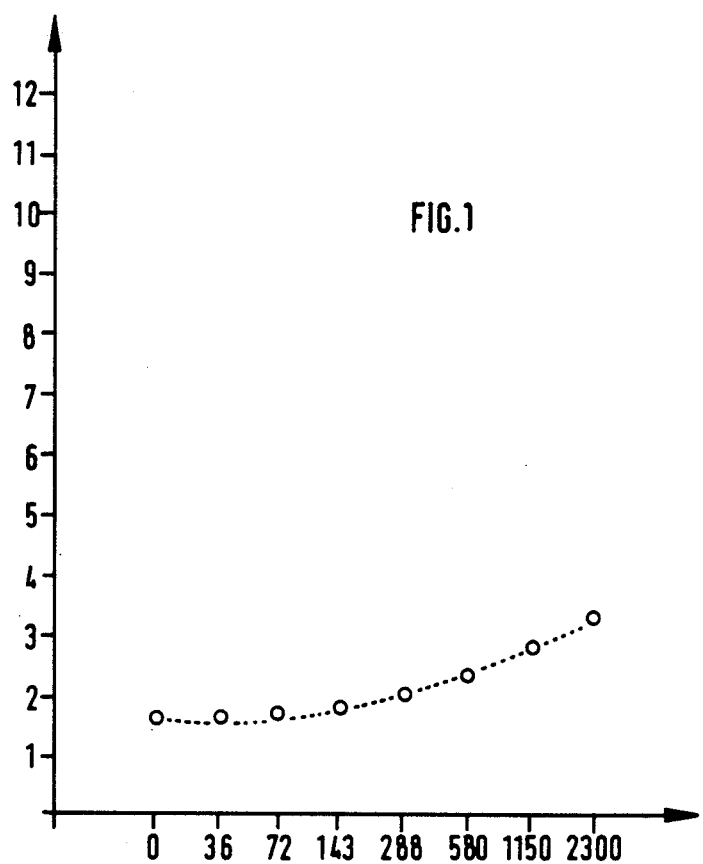

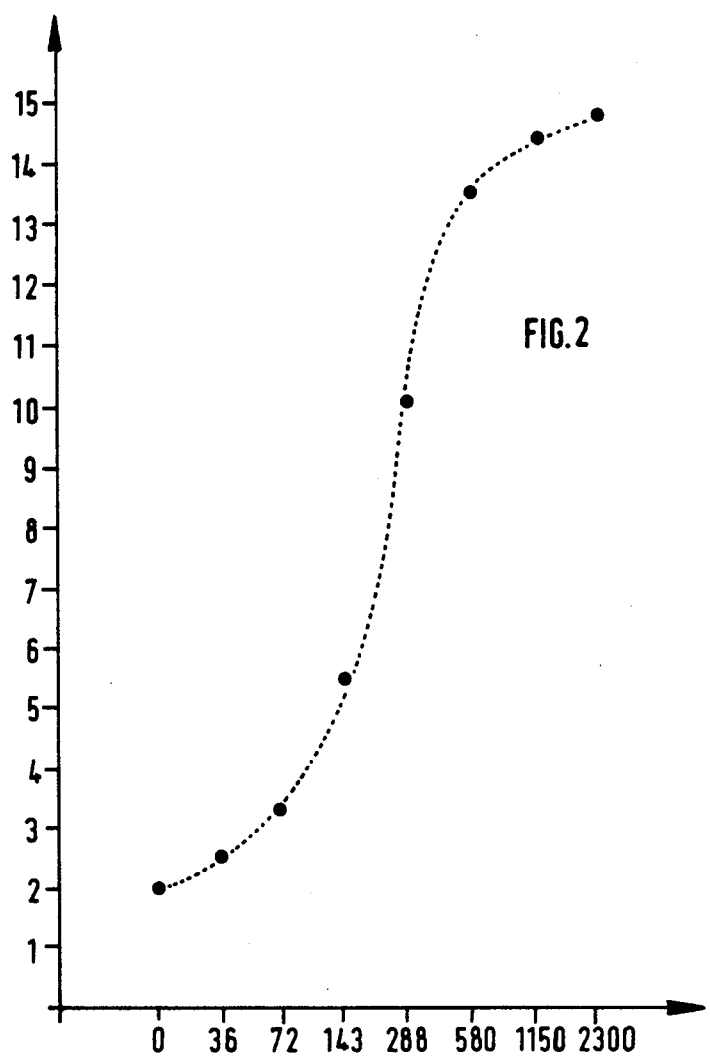

DISPERSION POLYMERS, AND THEIR USE

The invention relates to dispersion polymers, processes for their preparation and their use, the dispersion polymers consisting of latex particles which have been prepared by a seed polymerization process by a procedure in which the seed polymer used still has a content of 5 to 50% by weight of monomers which have not polymerized completely and the seed polymerization is carried out with monomers, at least one monomer being a compound containing acetal groups.

Biologically active dispersion polymers are obtained therefrom by binding biologically active substances which have free amino groups to reactive groups derived from the aldehyde function which are present on the surface of the dispersion polymer particles according to the invention. These biologically active latex conjugates are suitable for serological or immunological determination methods.

It is known that the sensitivity of serological or immunological determination methods can be increased by using indicator or carrier particles charged with the corresponding immunological reagent. Examples of carriers which can be used are red blood corpuscles or cells of a cell culture. Latex particles with a diameter of 0.02 to 5 μm are also used for this purpose.

Latex particles which contain acetal functions bonded via acid amide groups are known from European Patent Application No. EP-A 82110273.8. Latex cores previously prepared in an aqueous medium are swollen with vinyl monomers containing acetal functions bonded via acid amide groups, and these vinyl monomers, which must be sufficiently water-insoluble, are then copolymerized together with other monomers, which may be hydrophilic or ionic in nature. Such reagents can be used for the nephelometric and turbidimetric determination of proteins.

For this purpose, antibodies against the protein to be determined are bonded to the latex. After appropriate dilution of the latex charged with antibodies, the reagent thus formed can be used for measurement: after incubation with the antigen to be determined, agglutinates which can be measured nephelometrically or turbidimetrically are formed. The resulting scattered light signals according to this prior art are quite low and therefore do not allow a readily reproducible measurement. An increase in the detection sensitivity of the reagent and also ar associated increase in the scattered light signals during the reaction between a reagent according to the prior art and the antigen to be detected cannot be achieved easily.

It has now been found, surprisingly, that the disadvantages described for the prior art can be overcome by using carrier particles which are prepared by a method which comprises using previously prepared latex cores which have not polymerized completely and which still contain a considerable proportion of the non-polymerized monomers employed, that is to say which have a high residual monomer content, and co-polymerizing these latex cores which have not polymerized completely and are thus swollen in the monomer, for example styrene, with acrylic or methacrylic monomers containing acetal groups bonded via acid amide groups, if appropriate together with acrylic or methacrylic acid monomers, in an aqueous medium.

The invention thus relates to dispersions which contain latex carrier particles which have been prepared by the seed dispersion process in which only 30–90% by weight, preferably 40–80% by weight, of the monomers present have polymerized completely in the seed latex used, and on the surface of which is a copolymer which has been polymerized from a monomer mixture which contains monomers of the formula I

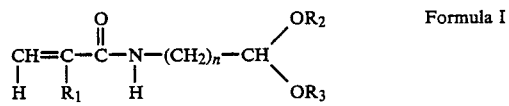  Formula I in which n=1–6;
$R_1$=H or $CH_3$ and
$R_2$ and $R_3$ are identical or different, where
$R_2$ and $R_3$=—$(CH_2)_m$—$CH_3$, and m=0–7, or

in which X, Y and Z=$(CH_2)_p CH_3$ and p=1–3,
where X, Y and Z are identical or different,
or $R_2$ and $R_3$=an aryl radical,
and if appropriate crotonic and/or acrylic and/or methacrylic acid, and if appropriate the monomer from which the seed polymers are formed, that is to say, for example, styrene.

The invention furthermore relates to a process for the preparation of the dispersions, which comprises first preparing a latex dispersion seed by polymerizing monomers, such as, for example, styrene, such that only 30–90% by weight of the monomers employed have polymerized completely, and subsequently separating off the excess monomer which is not dissolved in the polymer by filtration or by extensive dialysis and then adding a monomer mixture and polymerizing this on. This mixture contains compounds with terminal acetals of the formula I and if appropriate crotonic and/or acrylic and/or methacrylic monomers, as well as monomers from which the seed polymer is formed, for example styrene. The seed latex is preferably polymerized by polymerizing only 40–80% (w:w) of the monomers present completely. A polymerization process for which 50–70% (w:w) of the monomers present have polymerized completely is preferred for the seed latex.

Polymer cores which still contain 5–50% by weight of monomer, based on the polymer, are thus obtained by the process according to the invention. Preparations which contain 10–40% by weight of monomer, based on the polymer, are preferred. Preparations which contain 20–30% by weight of monomer, based on the polymer, are particularly preferred.

The latex particles used as the seed dispersion for the dispersions according to the invention should be polymers which are not film-forming. By "not film-forming" there are understood polymer latex particles which do not form a film and do not coalesce under the use conditions. Polymers of carbocyclic aromatic monovinylidene monomers, such as styrene, vinyltoluene and vinylnaphthalene, and mixtures of these monomers with one another and/or with methyl methacrylate and acrylonitrile are preferred. Particularly preferred seed dispersions are polystyrene latices. A polystyrene seed dispersion is prepared by processes which are known per se.

To prepare the dispersion polymer according to the invention, about 20–80% (w:w) of the amount of an emulsifier which would be required for maximum monomolecular cover of the latex surface is in principle added to a previously prepared latex with a particle diameter of 0.02 to 2 μm, preferably 0.05 to 0.5 μm. Measurements for the determination of the amount of emulsifier which leads to maximum cover of the latex surface are carried out with the aid of a tensiometer. They have been published, for example, by I. Phrma and S.-R. Chen in Journal of Colloid and Interface Science, Volume 74 (1979), pages 90–102 and for the first time by S. H. Maron, M. E. Elder and I. N. Ulevitch in Journal of Colloid Interface Sciences, Volume 9 (1954), pages 89–104.

Examples of possible emulsifiers are polyglycol ethers with long-chain aliphatic alcohols which preferably contain 10–20 carbon atoms, or alkylphenol, the alkyl radical of which preferably contains 6–12 carbon atoms, or dialkylphenol or trialkylphenol, the alkyl radicals of which are preferably branched alkyl radicals with in each case 3–12 carbon atoms. Examples of these are reaction products of ethylene oxide with lauryl alcohol, stearyl alcohol, oleyl alcohol, coconut fatty alcohol, octylphenol, nonylphenol, diisopropylphenol, triisopropylphenol, di-t-butylphenol and tri-t-butylphenol. Reaction products of ethylene oxide with polypropylene glycol are also suitable.

Suitable ionic emulsifiers are above all anionic emulsifiers, in particular alkali metal or ammonium salts of alkylsulfonates or alkylarylsulfonates and of the corresponding sulfates, phosphates or phosphonates, which optionally contain oxyethylene units between the particular hydrocarbon radical and the anionic group. Examples of these are sodium dodecyl-sulfate, sodium lauryl-sulfate, sodium octylphenol glycol ether-sulfate, sodium dodecylbenzenesulfonate, sodium lauryl diglycol-sulfate, ammonium tri-t-butylphenol pentaglycol-sulfate and ammonium tri-tbutylphenol octaglycol-sulfate. Sodium dodecyl-sulfate is preferably employed.

A monomer mixture which contains at least one compound of the formula I containing acetal groups is added dropwise, with stirring, to the seed dispersion which, in addition to the emulsifier, contains a free radical starter (initiator). The temperature of the dispersion is between 10° C. and +120° C., preferably between +50° C. and +90° C.

The polymerization is carried out by processes which are known per se in the presence of an initiator which forms free radicals, for example a peroxide compound or an aliphatic azo compound. The initiator is water-soluble; it is employed in an amount of 0.05 to 10% by weight, preferably 0.1 to 3% by weight (based on the total amount of the monomers). Examples of known initiators which form free radicals are hydrogen peroxide, alkali metal or ammonium salts of peroxydisulfuric acid or peroxydiphosphoric acid, for example sodium peroxydisulfate, potassium peroxydisulfate and ammonium peroxydisulfate, and furthermore alkyl hydroperoxides, such as t-butyl hydroperoxide, dialkyl peroxides, such as di-t-butyl peroxide, diacyl peroxides, such as diacetyl peroxide, dilauroyl peroxide and dibenzoyl peroxide, as well as azodiisobutyronitrile, azo-dicarboxamide and azo-gamma,gamma'-bis(4-cyanovaleric acid). The alkali metal or ammonium salts of peroxydisulfuric acid, such as sodium, potassium and ammonium peroxydisulfate, are preferably employed.

If appropriate, the initiator is used together with a reducing agent, in particular with an alkali metal salt or alkaline earth metal salt of a reducing sulfur-containing acid; compounds which are preferably suitable are sulfites, bisulfites, pyrosulfites, dithionites, thiosulfates and formaldehyde-sulfoxylates. Glucose and ascorbic acid can also similarly be used.

The compounds of the formula I are used as monomers containing acetal groups, and an acryl- or methacrylamidoalkylaldehyde di-alkyl acetal where alkyl=$C_2$ to $C_8$ is preferably used. Acryl- or methacrylamidoacetaldehyde di-n-pentyl acetal is especially suitable.

Up to 30% by weight, based on the total mixture, of styrene, vinylnaphthalene or vinyltoluene can be added to the monomer mixture containing a compound of the formula I. If appropriate, the monomer mixture can also additionally contain up to 30% by weight, based on the total mixture, of methacrylic acid, acrylic acid or crotonic acid.

The monomer mixture is added to the seed dispersion in amounts 90 to 5% by weight; preferably 40 to 10% by weight, based on the total amount of the seed dispersion and monomer mixture.

It may be important for successful polymerization in the presence of the seed polymer for the monomer mixture to be added dropwise with continuous stirring to the suspension of the latex cores under polymerization conditions, that is to say at a temperature of +10° C. to +120° C., preferably +50° C. to +90° C. During the dropwise addition, the amount of monomers added is continuously attracted to the already finished seed latex particles and is polymerized onto these to form further polymer around the latex particle.

The polymer is then freed from excess monomers, residues of the initiator and the emulsifier by known processes. The polymer is advantageously subjected to dialysis, for example against $NaHCO_3$ buffer (0.01 to 0.05% by weight).

To prepare the biologically active dispersions according to the invention, also called latex conjugates below, a suspension of the latex particles polymerized by seed polymerization in the manner described above is brought to a pH of less than 5, preferably less than 3, and incubated with the immunologically active material to be bound, such as, for example, antibodies, antigens or haptens. The unstable bonds between an amino group of the protein and the aldehyde liberated on the latex particle according to the invention are reduced by known processes. A solution of sodium cyanoborohydride in neutral buffer is preferably used for this. Any non-bound immunologically active material or other impurities are removed from the reaction mixture. This is advantageously effected by centrifugation or washing on suitable membranes.

The seed-polymerized latices according to the invention are distinguished by a particularly high stability. They are suitable for the preparation of sensitive reagents. The reagents according to the invention can be dried by lyophilization.

BRIEF DESCRIPTION OF THE DRAWINGS

FIG. 1 shows nephelometric measurement as in the prior art.

FIG. 2 shows nephelometric measurement according to the invention.

Reagents prepared according to the prior art stow, on nephelometric or turbidimetric measurement, a reaction with the antigen to be detected, with agglutination and thus an increase in the scattered light signal or the extinction in the measurement cell. Thus, for example, a reagent for the determination of C-reactive protein, an important inflammation parameter, has been prepared using rabbit antibodies against C-reactive protein (CRP). If this reagent is reacted with different CRP concentrations and the scattered light signals are measured in a nephelometer after an incubation time of 30 minutes, a standard curve which shows higher scattered light signals as the CRP concentration increases is obtained. Such a standard curve is shown in FIG. 1. It can be clearly seen that only low scattered light signals can be measured for the CRP concentrations employed. Associated with this is a low sensitivity of the measurement, the lower detection limit of the reagent being about 288 pg/liter CRP; that is to say CRP concentrations in the range between 36 µg/liter and 288 pg/liter can not be detected.

The reagent according to the invention, prepared by binding antibodies, for example against CRP, to latex preparations obtained by seed polymerization on polymers which contain residual monomers and have not polymerized completely exhibits, on the other hand, a much stronger agglutination reaction after reaction with CRP. If this reagent according to the invention is reacted with different CRP concentrations and the scattered light signals are measured in a nephelometer after an incubation time of 30 minutes, a standard curve which already shows high scattered light signals at low CRP concentrations is obtained. Such a standard curve is shown in FIG. 2. It can be seen that the sensitivity of the reagent is so high that even low CRP concentrations down to 36 µg/liter can be measured. Furthermore, the scattered light signals for CRP concentrations of between 36 and 2,300 µg/liter are very much higher than for a reagent according to the prior art. This means that the reproducibility of the measurement is very much better than that according to the prior art.

Other reagents according to the invention with corresponding advantageous properties are obtained if the latex preparations according to the invention are charged, for example, with antibodies against alpha-fetoprotein (AFP), ferritin, human placental lactogen (HPL), thyroxin-binding globulin (TBG), immunoglobulin E, $\beta_2$-microglobulin, pregnancy-specific $\beta_1$-glycoprotein and human chorionic gonadotropin ($\beta$HCG).

Monoclonal antibodies can also advantageously be used for the preparation of the reagents according to the invention. Latex preparations can similarly be charged with bacterial or viral proteins, such as, for example, streptolysin O, streptococcus B antigen, H. influenza antigen, pneumococcus antigen, lues antigen, toxoplasma antigen, HBsAg, rubella antigen, herpes antigen and tetanus antigen, and the corresponding antibodies can be detected by these antigencharged reagents according to the invention.

Finally, latex preparations according to the invention can be charged in the same manner with derivatized haptens, for example hormones or medicaments, such as thyroxin ($T_4$), triiodothyronine ($T_3$), cortisol, progesterone, testosterone, gentamycin and digoxin, giving biologically active dispersion polymers. The reagents according to the invention, with which the concentration of the haptens mentioned can be measured are used by inhibition tests, that is to say by simultaneous use of suitable antibodies.

The latex preparations according to the invention are easy to prepare and to link with sensitive immunologically active materials under gentle conditions to give a diagnostic reagent.

The latex conjugates can be used in all diagnostic methods which measure changes in particle size, for example in qualitative and semi-quantitative determinations of substances with the aid of visual latex agglutination tests and in nephelometric or turbidimetric determinations of trace proteins in the direct or competitive agglutination test or in the latex-hapten inhibition test.

EXAMPLES

1. Preparation of the seed polymer 310 ml of doubly-distilled water saturated with nitrogen were introduced into a cylindrical glass vessel equipped with a gas inlet and gas outlet tube and a magnetic stirring rod. 500 mg of sodium stearate were added and were dissolved by stirring. 1.5 ml of 25% strength ammonia were also added. The pH was checked and was 11.09. The polymerization vessel was freed from oxygen by evacuating and filling with nitrogen several times. The detergent solution was warmed to +70° C. with the aid of a waterbath, while stirring continuously. 90 ml of freshly distilled styrene were then introduced under nitrogen with the aid of a dropping funnel with pressure compensation into the polymerization vessel. The mixture was stirred at +70° C. for 15 minutes to emulsify the styrene. The temperature was then raised to +90° C. and the mixture was stirred for a further hour. 67.5 mg of potassium peroxydisulfate, dissolved in 50 ml of distilled water saturated with nitrogen, were then added. The mixture was stirred at +90° C. for 80 minutes. The polystyrene was added through a folded filter. Under certain circumstances, a few ml of styrene remain on the filter during this operation. This styrene could not be dissolved completely in the polystyrene, because some excess of styrene was present.

The filtered polystyrene was dialyzed against 10 liters of 0.01%(w:w) strength ammonium bicarbonate solution (with 0.01%(w:w) of $NH_4HCO_3$; 0.01% by weight of $NaN_3$; brought to pH 10.0 with 10.5 ml of 25% strength by weight ammonia in 10 liters) for 50 hours. After the dialysis, 410 ml of polymer with a dry weight of 12.8 g/dl were obtained. About 60% of the monomer employed had thus been polymerized. It was possible to increase the content of the polymerized styrene by increasing the polymerization time by 5 to 10 minutes, the monomer dissolved in the polystyrene being simultaneously reduced.

On the other hand, it was possible to reduce the content of styrene which had polymerized completely by reducing the polymerization time by 5 to 10 minutes; the monomer dissolved in the styrene being simultaneously increased.

2. Seed polymerization using the polymer prepared according to Example 1

156.3 ml of a polystyrene latex dispersion with a solids content of 12.8% by weight, 238.7 ml of distilled water and 250 mg of sodium dodecyl-sulfate were introduced into a cylindrical glass vessel equipped with a gas inlet and gas outlet tube and a magnetic stirring rod and were dissolved by stirring. The polymerization vessel was freed from oxygen by evacuating and filling with nitrogen several times. The latex detergent mixture was heated to +70° C. in a waterbath, while stirring continuously.

A monomer mixture prepared from 2 ml of styrene, 2 ml of methacrylamidoacetaldehyde di-n-pentyl acetal and 1 ml of methacrylic acid was added under nitrogen. The mixture was then emulsified at about 20° C. for 1 hour, while stirring.

The polymerization batch was then warmed to +70° C. in a waterbath. After being stirred at +70° C. for 15 minutes, the copolymerization was started. For this, 5 ml of a potassium peroxydisulfate solution (16 mg/ml in distilled water) were added. The temperature of the polymerization batch was kept at +70° C. The mixture was stirred at the above temperature for 5 hours. The polymerization was thus ended and the dispersion was cooled to room temperature and filtered through a folded filter. 395 ml of a latex suspension were obtained. This was then dialyzed against an NaHCO$_3$ buffer solution (0.25 g/liter, pH 8–8.2) for 17 hours. 415 ml of a latex dispersion with a solids content of 6.8% by weight were obtained.

3. Binding of anti-CRP antibodies to a polymer according to the invention

Anti-CRP antibodies were bound to a polymer prepared according to Example 2. The polymer used was diluted to a solids content of 5.8% by weight with distilled water. An antiserum obtained by immunization of rabbits with purified CRP was isolated as the gamma-fraction by known methods. It was then concentrated until a protein content of 10 mg/ml was reached. 0.5 ml of the abovementioned polymer was mixed with 0.05 ml of the anti-CRP antibody solution. 0.025 ml of a 20% strength aqueous solution of eicosaoxyethylene sorbitan laurate (Tween ®20) was then added and all the components were mixed again. 0.01 ml of 1 N HCl was added to this, so that the pH value reached about 2. After an incubation time of 30 minutes at room temperature, 0.125 ml of saturated aqueous sodium hydrogen phosphate solution (pH 6.5) and 0.125 ml of aqueous sodium cyanoborohydride solution (25 mg/ml) were added and the components were mixed thoroughly. The mixture was then incubated at room temperature for one hour.

This preparation was then centrifuged at about 50,000 g for 30 minutes (Beckman centrifuge, 20,000 rpm). The supernatant was discarded. The residue was resuspended in 0.75 ml of a glycine-NaCl buffer (0.1 mol of glycine, 0.17 mol of NaCl, 0.5% (w:w) of eicosaoxyethylene sorbitan laurate (Tween ®20), pH 8.2).

The mixture was then subjected to ultrasonic treatment (Bronson Sonyfier B 15) for 2 seconds. The reagent redispersed in this way was diluted with the abovementioned glycine-NaCl buffer in a volume ratio of 1:80 and treated with ultrasound again for 30 seconds.

4. Measurement of CRP concentrations in serum samples

The reagent for determination of CRP which was prepared according to Example 3 by binding anti-CRP antibodies to latex preparations according to the invention was used to measure CRP in patient sera. The LN-CRP standard (human) (Behringwerke AG) was used as the standard. According to the pack leaflet, this CRP standard contained 86 mg/liter of CRP. The standard was first diluted to 2.3 mg/liter in glycine-sodium chloride buffer (0.1 mol of glycine, 0.17 M NaCl, pH 8.2) and then further diluted stepwise to twice the volume each time. A standard series of decreasing CRP concentrations was thus obtained. For measurement, 10 μl of standard serum dilution were mixed with 150 μl of a reactive buffer (0.1 mol of glycine, 0.17 mol of NaCl, 4%(w:w) of polyethylene glycol (PEG) 6000,0.5%(w:w) of eicosaoxyethylene sorbitan laurate (Tween ®20), pH 8.2) and 50 μl of the reagent according to Example 3 in BLN cells (Behringwerke AG) and the mixture was incubated at room temperature for 30 minutes. The cells were then measured in a laser nephelometer (Behringwerke AG). The reference curve for measurement of the standard sera was plotted on semilogarithmic paper and the measured values for the patient sera were evaluated on this curve. A typical reference curve is shown in FIG. 2.

I claim:

1. A dispersion polymer which contains latex particles having an incompletely polymerized monomer content of 5 to 50% by weight, based on the latex particles, on the surface of said latex particles is a copolymer of a monomer mixture which contains at least one of the compounds of the formula I containing acetal groups.

2. A dispersion polymer as claimed in claim 1, in which the latex particle is a polystyrene latex.

3. A dispersion polymer as claimed in claim 1, in which the incompletely polymerized monomer content is about 10 to 40% by weight, based on the polymer.

4. A dispersion polymer as claimed in claim 1, wherein the monomer of formula I is an acryl- or methacrylamidoalkylaldehyde di-alkyl acetal in which alkyl is $C_2$ to $C_8$.

5. A dispersion polymer as claimed in claim 1, wherein the monomer of formula I is methacrylamidoacetaldehyde di-n-penyl acetal.

6. A biologically active dispersion polymer comprising a dispersion polymer as claimed in claim 1, which is bonded to an active substance selected from the group consisting of an antibody, an antigen and a hapten.

7. A diagnostic agent which contains a biologically active dispersion polymer comprising a dispersion polymer as claimed in claim 1 which is bonded to an active substance selected from the group consisting of an antibody, an antigen and a haptan.

8. The dispersion polymer of claim 1, wherein the monomer mixture further contains at least one monomer selected from the group consisting of crotonic acid, acrylic acid, methacrylic acid and a carbocyclic aromatic monovinylidene monomer.

* * * * *

UNITED STATES PATENT AND TRADEMARK OFFICE
CERTIFICATE OF CORRECTION

PATENT NO. : 4,962,046
DATED : October 09, 1990
INVENTOR(S) : Wolfgang Kapmeyer

It is certified that error appears in the above-identified patent and that said Letters Patent is hereby corrected as shown below:

Title Page, Title change "DISPERSION POLYMERS, AND THEIR USE" to --DISPERSION POLYMERS--

Title page,

Abstract, line 13, before "or $R_2$ and $R_3$ = an aryl radical" insert --in which X,Y, and Z = $(CH_2)_p -CH_3$ and p= 1-3, where X,Y, and Z are identical or different, --

Drawings, Figures 1 and 2, above the vertical axes, insert -- relatives Streulichtsignal (v) -- and below the horizontal axes insert -- Kozentration CRP in ug/l Column 1, line 1, change "DISPERSION POLYMERS, AND THEIR USE" to --DISPERSION POLYMERS--

UNITED STATES PATENT AND TRADEMARK OFFICE
CERTIFICATE OF CORRECTION

PATENT NO. : 4,962,046

DATED : October 9, 1990

INVENTOR(S) : Wolfgang Kapmeyer

It is certified that error appears in the above-identified patent and that said Letters Patent is hereby corrected as shown below:

Claim 1, column 8, line 29 after "groups" insert

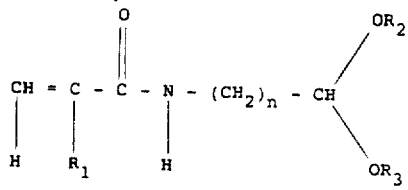

wherein N is 1-6;

$R_1$ is H or $CH_3$ ; and $R_2$ and $R_3$ are identical or different, where $R_2$ and $R_3$ are $(CH_2)_m - CH_3$, and m is 0-7, or 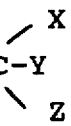 in which X,Y and Z are $(CH_2)_p -CH_3$ and cap p is 1-3, where X,Y and Z are identical or different, or $R_2$ and $R_3$ are an aryl radical.--

UNITED STATES PATENT AND TRADEMARK OFFICE
CERTIFICATE OF CORRECTION

PATENT NO. : 4,962,046

DATED : October 9, 1990

INVENTOR(S) : Wolfgang Kapmeyer

It is certified that error appears in the above-identified patent and that said Letters Patent is hereby corrected as shown below:

Column 8, line 50, change "haptan" to --hapten--

Signed and Sealed this

Fifteenth Day of June, 1993

Attest:

MICHAEL K. KIRK

Attesting Officer     Acting Commissioner of Patents and Trademarks